US00PP32495P3

(12) United States Plant Patent
Forner-Giner

(10) Patent No.: US PP32,495 P3
(45) Date of Patent: Nov. 24, 2020

(54) ***CITRUS* TREE NAMED 'CIVAC 19'**

(50) Latin Name: ***Citrus* hybrid**
Varietal Denomination: Civac 19

(71) Applicants: Instituto Valenciano de Investigaciones Agrarias (IVIA), Valencia (ES); Agromillora Iberia, S.L., Barcelona (ES)

(72) Inventor: Maria Angeles Forner-Giner, Valencia (ES)

(73) Assignees: Instituto Valenciano de Investigaciones Agrarias (IVIA), Valencia (ES); Agromillora Iberia, S.L., Barcelona (ES)

( * ) Notice: Subject to any disclaimer, the term of this patent is extended or adjusted under 35 U.S.C. 154(b) by 0 days.

(21) Appl. No.: 16/873,255

(22) Filed: Mar. 5, 2020

(65) Prior Publication Data

US 2020/0288614 P1 Sep. 10, 2020

Related U.S. Application Data

(60) Provisional application No. 62/919,324, filed on Mar. 6, 2019.

(51) Int. Cl.
*A01H 5/00* (2018.01)
*A01H 6/78* (2018.01)

(52) U.S. Cl.
USPC ..... Plt./201
CPC ..... *A01H 6/785* (2018.05)

(58) Field of Classification Search
USPC ..... Plt./201
See application file for complete search history.

*Primary Examiner* — Annette H Para
(74) *Attorney, Agent, or Firm* — The Webb Law Firm

(57) ABSTRACT

A new and distinct variety of *Citrus* tree that can be used as a rootstock having a high fruit quality and a long harvest period.

6 Drawing Sheets

Botanical classification: *Citrus* hybrid.
Varietal denomination: 'Civac 19'.

BACKGROUND OF THE INVENTION

The present invention comprises a new and distinct variety of *Citrus* hybrid (*Citrus reshni* x *Poncirus trifoliata*) that can be used as a rootstock having the varietal name 'Civac 19'. The new variety is the result of a planned breeding program conducted in Valencia, Spain with the purpose of providing new *Citrus* rootstocks. The new variety is the result of a cross between an unpatented 'Cleopatra' mandarin (*Citrus reshni*) as the female parent and an unnamed and unpatented trifoliate orange (*Poncirus trifoliata*) as the male parent. 'Civac 19' was first asexually reproduced by micropropagation in April of 2000 in Barcelona, Spain and has been reproduced true to type over successive asexual reproductions. The leaves and fruits of the new variety are distinguishable from its female parent. The leaves of the new variety are similar to its male parent, but the fruits and tree size of 'Civac 19' are distinguishable from its male parent. The new variety has not been evaluated under all possible environmental conditions. The phenotype of the new variety may vary with variation in environment without a change in the genotype of the new variety.

The leaves and fruits of the new variety are similar to 'Carrizo' citrange (unpatented), but the seeds of the varieties differ. Further, the following traits distinguish 'Civac 19' as a new and distinct variety from other *Citrus* varieties known to the breeder:

1. Low vigor;
2. Weeping growth habit;
3. High fruit quality; and

4. Long harvest period due to the persistence of fruit on the tree.

DESCRIPTION OF THE DRAWINGS

With the exception of FIG. 6 (taken at approximately 3-4 months of age), the accompanying photographic images illustrate the new variety at approximately twenty years of age, with the colors being as nearly true as is possible with color illustrations of this type.

DESCRIPTION OF THE PLANT

Figure 1:
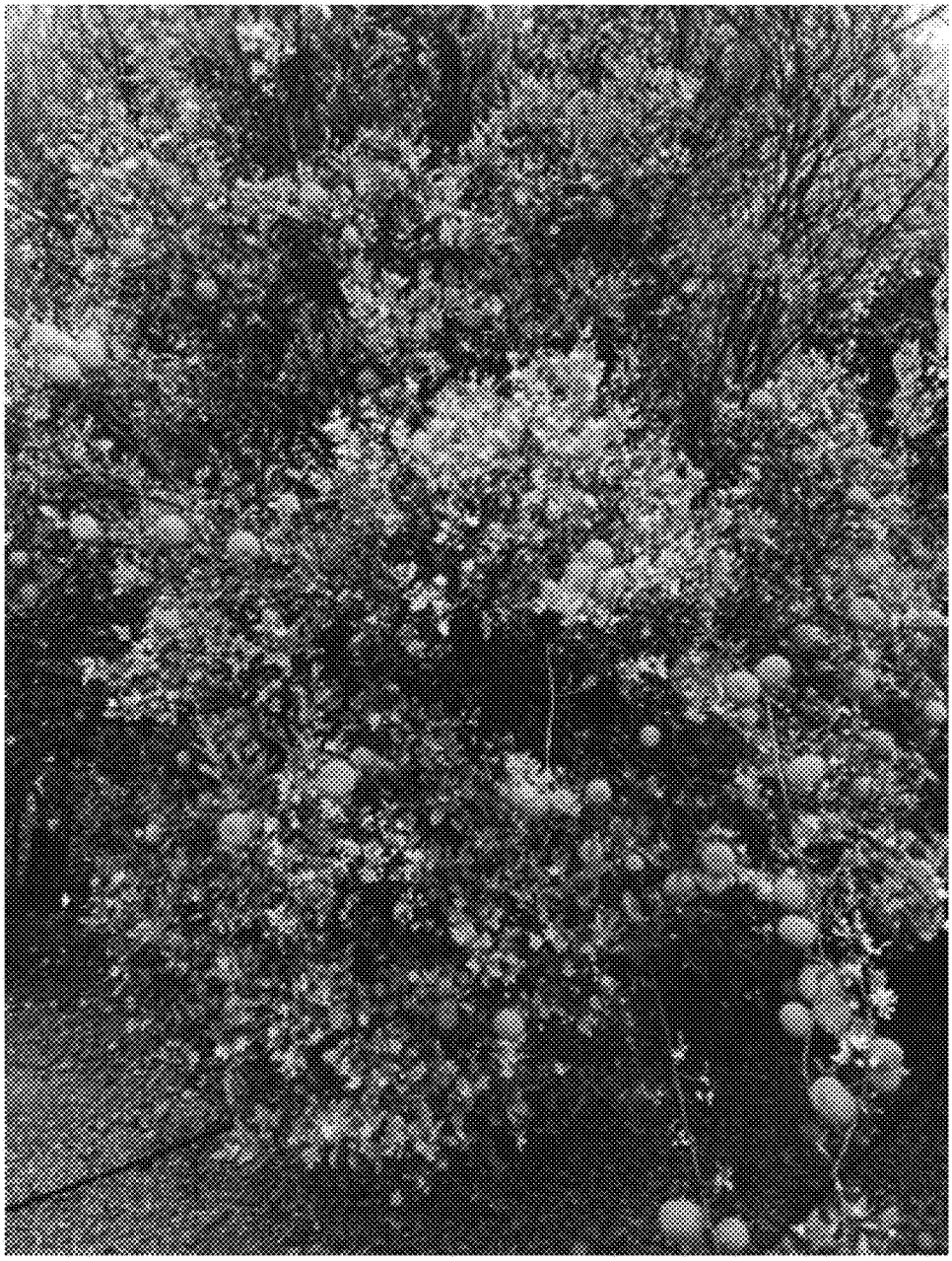
FIG. 1 illustrates a fruiting tree of the new variety.
Figure 2:
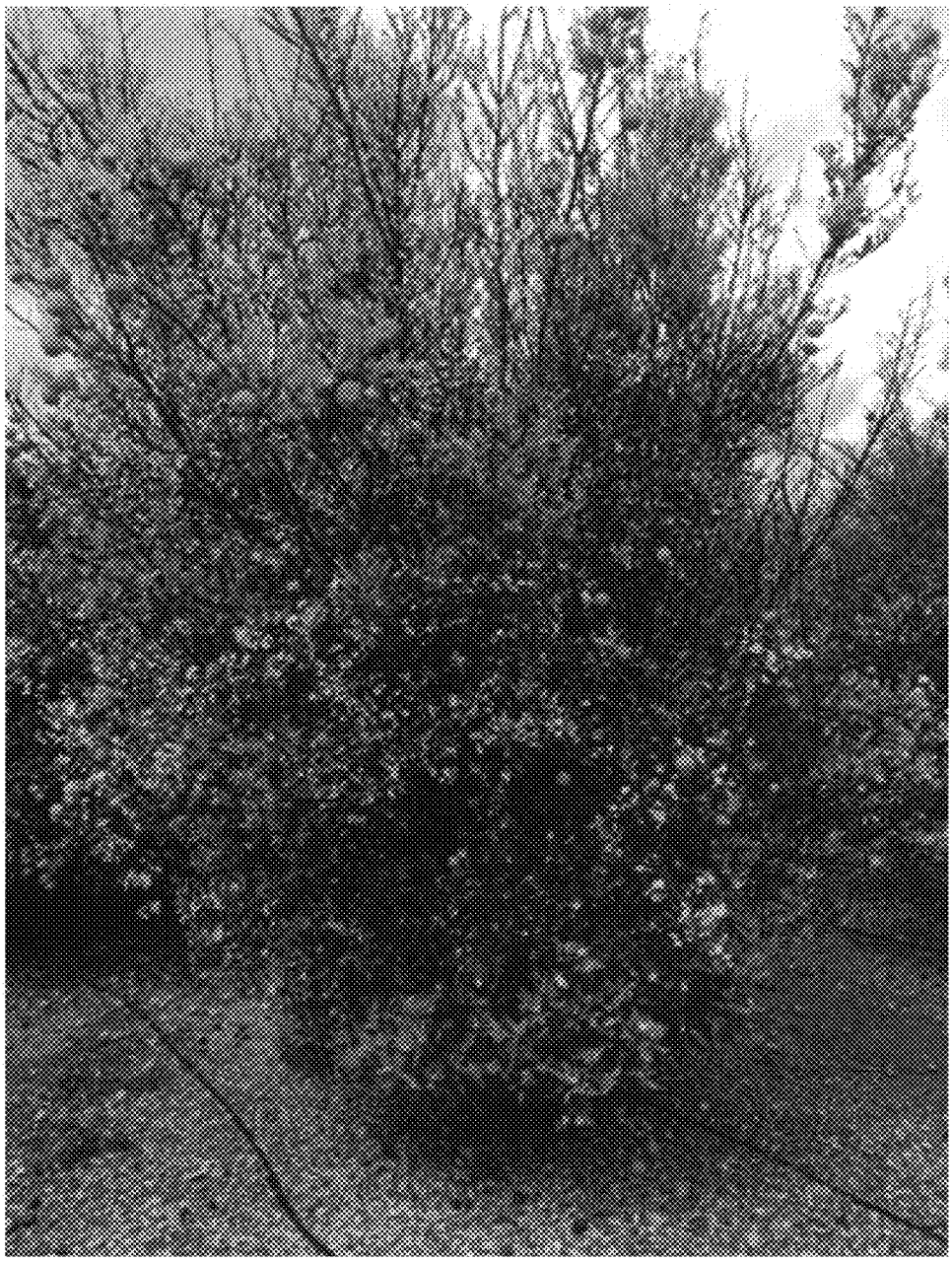
FIG. 2 illustrates a fruiting tree of the new variety.
Figure 3:
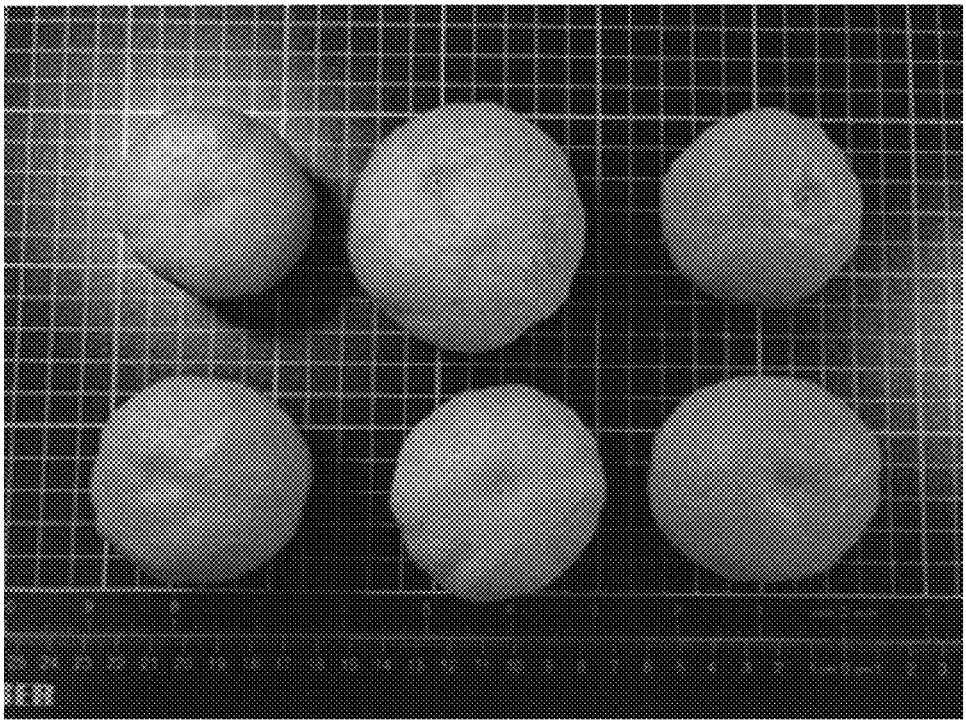
FIG. 3 illustrates the fruits of the new variety.
Figure 4:
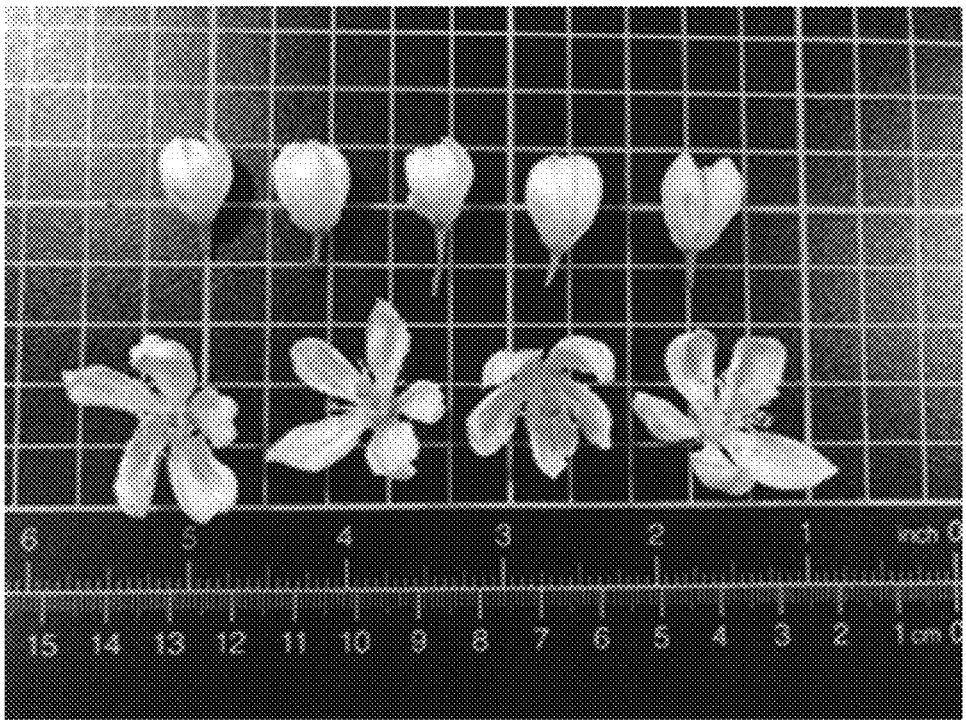
FIG. 4 illustrates the flowers of the new variety.
Figure 5:
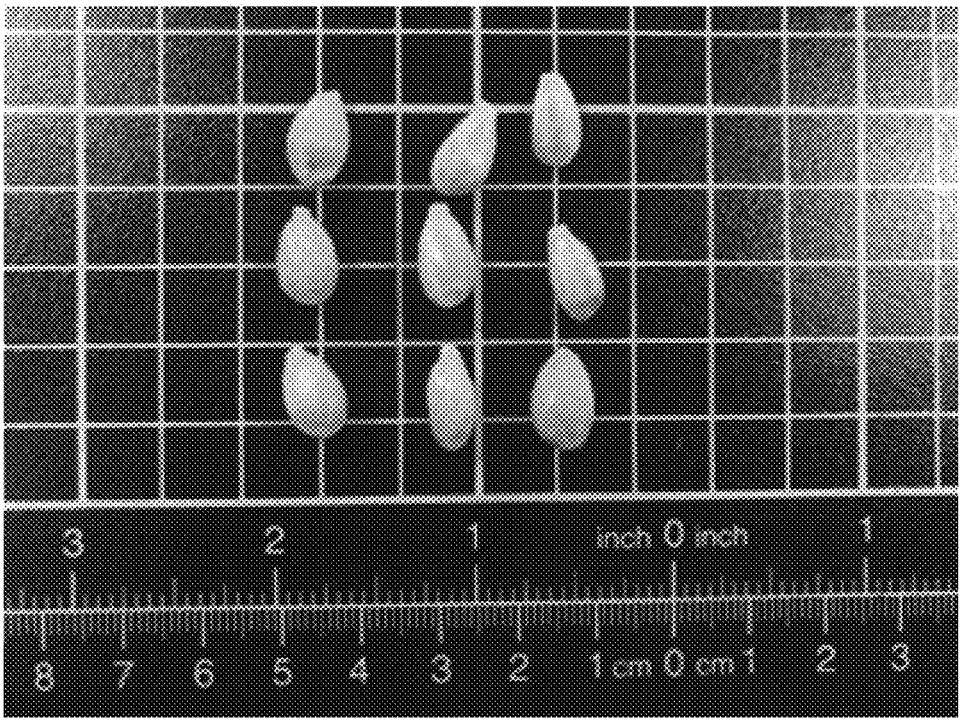
FIG. 5 illustrates the seeds of the new variety.
Figure 6:
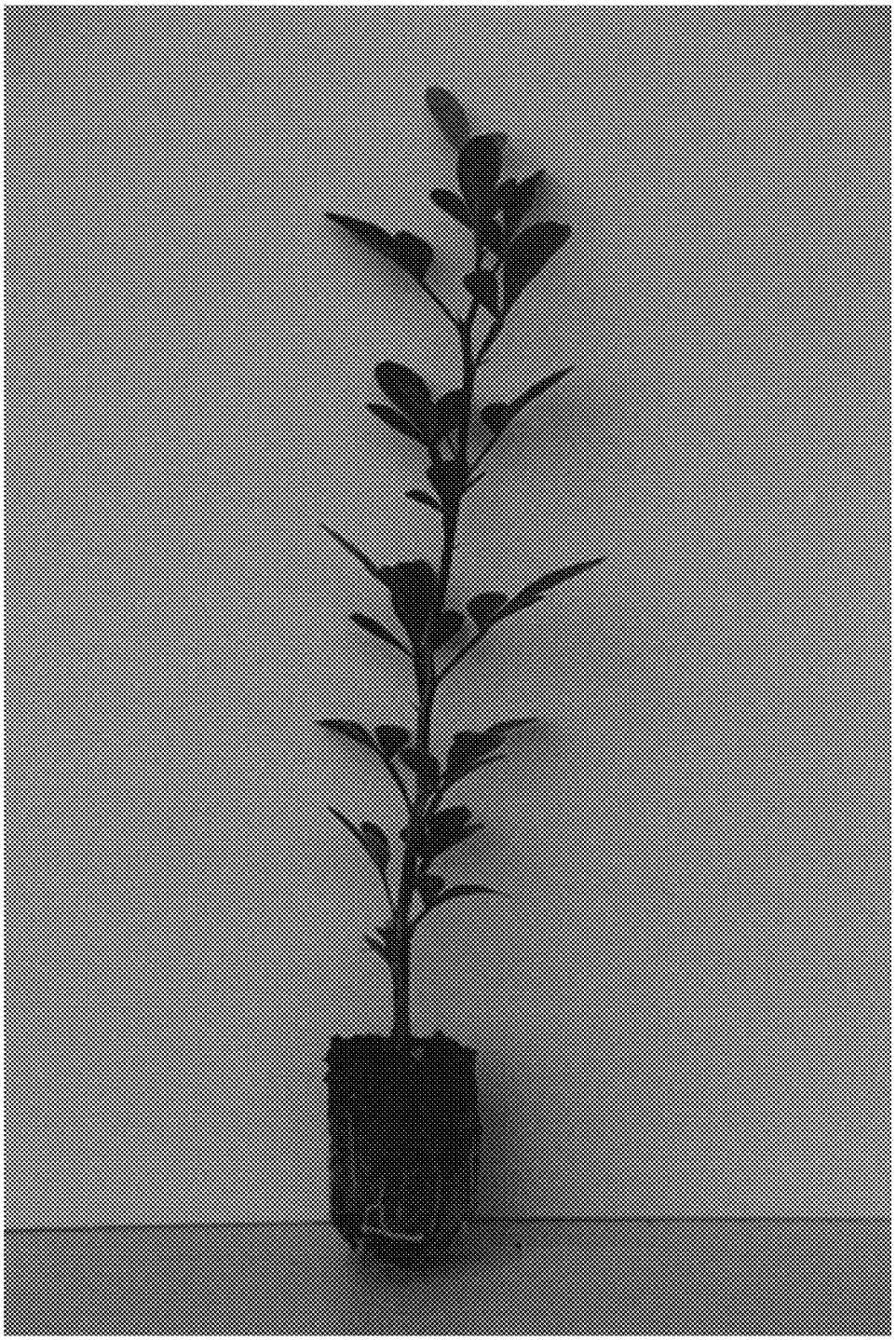
FIG. 6 illustrates a nursery plant of the new variety.

The following detailed description sets forth the characteristics of the new variety. The color readings and measurements were taken in Valencia, Spain under natural light on approximately twenty year old plants grown in open field conditions. Color references are primarily to The 2007 R.H.S. Colour Chart of The Royal Horticultural Society of London, $5^{th}$ Edition, except where general color terms are used.

PLANT

Time to initiate roots: About 10 days in vitro.
Time to develop roots: About 10 days in vitro.
Rooting description: Rustic and thick.

Overall tree shape: Upright.
Height: 5 m.
Spread: 3 m.
Growth rate: Medium.
Specific disease/pest resistance: Resistance to *Citrus tristeza* virus (CTV) and *Phytophthora*.
Cold temperature tolerance: Observed.
Heat tolerance: None observed.
Drought tolerance: None observed.
Trunk:
*Size*.—12 cm in diameter.
*Surface texture*.—Smooth.
*Bark color*.—195A.
*Lenticels*.—Length: 1.0 mm. Width: 0.5 mm. Color: 195D. Density: 0.5/cm$^2$.
Branches:
*Diameter*.—3.39+/−0.43 mm.
*Surface texture*.—Smooth.
*Color*.—146A.
*Form*.—Elliptical.
*Average angle*.—70°.
Leaves:
*Length*.—64.76+/−4.77 mm.
*Width*.—40.81+/−6.55 mm.
*Form*.—Composed of three leaflets.
*Texture*.—Smooth upper surface, rough lower surface.
*Thickness*.—0.60+/−0.10 mm.
*Base*.—Emargination at tip.
*Apex*.—Acute.
*Margin*.—Crenate incisions present.
*Pubescence*.—None present.
*Color*.—Young leaves: Upper surface: 144A. Lower surface: 144A. Mature leaves: Upper surface: 137A. Lower surface: 137C.
*Petiole*.—Shape: Wings absent. Length: 14.41+/−1.29 mm. Width: 1.65+/−0.24 mm. Color: 137A.
*Veins*.—Type: Pinnate. Upper surface color: 137A. Lower surface color: Medium green.
Flower buds:
*Pedicel*.—Length: 5.17+/−0.86 mm. Diameter: 0.95+/−0.26 mm. Color: 144A.
*Bud*.—Length: 14.15+/−1.60 mm. Width: 10.50+/−0.86 mm. Color: 144A.
Flowers:
*Bloom timing*.—March in Valencia, Spain.
*Blooming period*.—March to April in Valencia, Spain.
*Pollination requirements*.—None.
*Number of flowers per cluster*.—2 to 3.
*Fragrance*.—Orange blossom.
*Petals*.—Number: 5 per flower. Length: 16.10+/−1.65 mm. Width: 7.03+/−1.0 mm. Shape: Rounded. Aspect: Globose. Margin: Entire. Texture and appearance: Velvety. Color: When opening: Upper surface: 155A. Lower surface: 155A. Fully opened: Upper surface: NN155A. Lower surface: NN155A.
*Sepals*.—Shape: Acute. Margin: Smooth. Texture: Rough. Length: 3.88+/−0.25 mm. Width: 2.36+/−0.24 mm. Color: Upper surface: 154B. Lower surface: 154B.
Reproductive organs:
*Stamen*.—Number (per flower): 25.6+/−3.13 mm. Filament length: 7.30+/−0.39 mm. Filament color: 1A.
*Anther*.—Shape: Basifixed. Length: 1.84+/−0.13 mm. Color: 7A.
*Pollen*.—Color: 11A. Amount: Low.
*Pistil*.—Number (per flower): 1. Length: 7.39+/−0.84 mm.
*Style*.—Length: 2.37+/−0.18 mm. Color: 144D.
*Stigma*.—Shape: Capitate. Color: 154B. Ovary color: 144D.
Fruit:
*Average maturity/harvest date*.—January to February in Valencia, Spain.
*Average amount of fruit produced per season per tree*.—50.
*Persistence of fruit on tree*.—High.
*Storage quality*.—Very good.
*Shipping quality*.—Very good.
*Use*.—For seeds only.
*Weight*.—Average: 69.25+/−23.12 g. Minimum: 37.83 g. Maximum: 113.27 g.
*Shape*.—Overall: Slightly rounded. Apex: Without constriction at stalk end. Base: With presence of depression at distal end.
*Height*.—49.06+/−6.67 mm.
*Width*.—55.31+/−6.98 mm.
*Furrows*.—None present.
*Peduncle*.—Length: 6.61 mm. Width: 4.35 mm. Color: 144C.
*Rind*.—Surface texture: Rough, with no pubescence present. Color: N25B. Thickness: 4.36+/−0.66 mm. Adherence to flesh: Medium adherence. Ease of peeling: High. Oil glands: Present. Scent: *Citrus*.
*Flesh/pulp*.—Number of segments: 9+/−1. Separability of segments: High. Texture: Grainy. Vesicles: Average number per segment: 85. Shape: Cuneiform. Average length: 11.41+/−2.05 mm. Average width: 3.08+/−0.30 mm. Color: 21B. Scent: *Citrus*.
*Juice*.—Percentage amount per fruit: 18. Total soluble solids (degrees Brix): 12.3. Acidity (percentage): 5.2. Color: 16C. Scent: *Citrus*.
*Seeds*.—Average number per fruit: 20.8+/−10.13 mm. Shape: Ovate. Length: 12.93+/−0.5 mm. Width: 7.37+/−0.52 mm. Color: 10D.

I claim:

1. A new and distinct variety of *Citrus* tree, as is herein illustrated and described.

* * * * *